United States Patent [19]
Shapiro et al.

[11] Patent Number: 5,645,065
[45] Date of Patent: Jul. 8, 1997

[54] CATHETER DEPTH, POSITION AND ORIENTATION LOCATION SYSTEM

[75] Inventors: Alan R. Shapiro; Donald A. Kay, both of Sharon, Mass.

[73] Assignee: Navion Biomedical Corporation, Stoughton, Mass.

[21] Appl. No.: 420,020

[22] Filed: Apr. 11, 1995

Related U.S. Application Data

[63] Continuation-in-part of Ser. No. 755,024, Sep. 4, 1991, Pat. No. 5,425,367.

[51] Int. Cl.$^6$ ........................................... A61B 5/05
[52] U.S. Cl. ............................ 128/653.1; 128/899
[58] Field of Search ........................ 128/653.1, 899; 607/156

[56] References Cited

U.S. PATENT DOCUMENTS

| | | | |
|---|---|---|---|
| 2,321,355 | 6/1943 | Berman | 177/311 |
| 2,521,745 | 9/1950 | Pope | 177/311 |
| 2,820,959 | 1/1958 | Bell | 340/282 |
| 2,863,458 | 12/1958 | Modny et al. | 128/303 |
| 2,906,944 | 9/1959 | Lebourg | 324/34 |
| 2,908,863 | 10/1959 | Neff | 324/67 |
| 2,949,910 | 8/1960 | Brown et al. | 128/2.05 |
| 3,042,030 | 7/1962 | Read | 128/127 |
| 3,043,309 | 7/1962 | McCarthy | 128/348 |
| 3,190,290 | 6/1965 | Alley et al. | 128/348 |
| 3,253,588 | 5/1966 | Vuilleumier et al. | 128/2 |
| 3,452,742 | 7/1969 | Muller | 128/2 |
| 3,471,773 | 10/1969 | Penland | 324/3 |
| 3,547,103 | 12/1970 | Cook | 128/2.05 |
| 3,597,680 | 8/1971 | Haddon | 324/67 |
| 3,605,750 | 9/1971 | Sheridan et al. | 128/348 |
| 3,617,865 | 11/1971 | Hakata | 324/3 |
| 3,618,614 | 11/1971 | Flynn | 128/348 |
| 3,622,784 | 11/1971 | Del Guercio | 250/71.5 R |
| 3,623,101 | 11/1971 | Grebe et al | 343/112 R |
| 3,625,200 | 12/1971 | Muller | 128/20.5 R |
| 3,653,050 | 3/1972 | Eggleston. Jr | 343/112 D |
| 3,656,161 | 4/1972 | MacPherson | 343/200 PE |
| 3,659,588 | 5/1972 | Kahn et al. | 123/2 R |
| 3,661,148 | 5/1972 | Kolin | 128/2.05 P |
| 3,749,086 | 7/1973 | Kline et al. | 128/2 M |
| 3,749,134 | 7/1973 | Slinghluff et al. | 138/177 |
| 3,794,041 | 2/1974 | Frei et al. | 128/348 |
| 3,831,086 | 8/1974 | Pesto | 324/67 |

(List continued on next page.)

FOREIGN PATENT DOCUMENTS

| | | |
|---|---|---|
| 91577 | 10/1983 | European Pat. Off. . |
| 320623 | 6/1989 | European Pat. Off. . |
| 355996 | 2/1990 | European Pat. Off. . |
| 357397 | 7/1990 | European Pat. Off. . |
| 2432173 | 1/1976 | Germany . |
| WO88/00810 | 2/1988 | WIPO . |
| WO92/03090 | 5/1992 | WIPO . |

OTHER PUBLICATIONS

Starkhammar, H. et al., "Cath–Finder™ Catheter Tracking System . . . ", *Acta Anaesthesiol Scand* 1990: 34: 296–300.

Primary Examiner—Marvin M. Lateef
Assistant Examiner—Shawna Shaw
Attorney, Agent, or Firm—Cesari and McKenna

[57] ABSTRACT

A system for externally locating a sensor in tissue, comprising an external probe including at least first and second electromagnetic output coils with non-parallel longitudinal axes; and output coil driver for alternately energizing the first and second output coils, for generating a time-varying magnetic field which penetrates the patient's skin; a sensor coil, having a longitudinal axis, for developing an induced electrical voltage in response to the time-varying magnetic field; a distance determinator, responsive to the induced voltage from the sensor coil, for determining from the induced voltage, the distance between the output coils and the sensor coil, independently of the relative angle, in a horizontal plane, between the sensor coil longitudinal axis, and the longitudinal axes of the output coils; and a direction determinator for determining and displaying the direction, in the horizontal plane, in which the sensor coil longitudinal axis is pointing.

40 Claims, 10 Drawing Sheets

U.S. PATENT DOCUMENTS

| | | | |
|---|---|---|---|
| 3,836,842 | 9/1974 | Zimmermann et al. | 324/34 R |
| 3,847,157 | 11/1974 | Caillouette et al. | 128/348 |
| 3,878,453 | 4/1975 | Potter et al. | 324/3 |
| 3,885,561 | 5/1975 | Cami | 128/214 |
| 3,922,378 | 11/1975 | Kline | 427/2 |
| 3,932,805 | 1/1976 | Abe et al. | 324/0.5 A |
| 3,961,632 | 6/1976 | Moossun | 128/347 |
| 3,973,556 | 8/1976 | Fleischhacker et al. | 128/2 M |
| 3,975,735 | 8/1976 | McCullough et al. | 343/112 R |
| 3,978,863 | 9/1976 | Fettel et al. | 128/348 |
| 3,990,003 | 11/1976 | Agee, Jr. | 324/52 |
| 4,020,829 | 5/1977 | Willson et al. | 128/2 M |
| 4,080,706 | 3/1978 | Heilman et al. | 29/173 |
| 4,173,228 | 11/1979 | Van Steenwyk et al. | |
| 4,176,662 | 12/1979 | Frazer | 128/6 |
| 4,244,362 | 1/1981 | Anderson | 128/200.26 |
| 4,248,236 | 2/1981 | Linder | 128/349 B |
| 4,317,078 | 2/1982 | Weed et al. | 324/208 |
| 4,344,436 | 8/1982 | Kubota | 128/350 R |
| 4,379,261 | 4/1983 | Lakin | 324/240 |
| 4,402,328 | 9/1983 | Doring | 128/785 |
| 4,405,314 | 9/1983 | Cope | 604/51 |
| 4,416,289 | 11/1983 | Bresler | 128/737 |
| 4,431,005 | 2/1984 | McCormick | 128/656 |
| 4,432,369 | 2/1984 | Halvorsen | 128/653 |
| 4,445,089 | 4/1984 | Harrison | 324/238 |
| 4,445,501 | 5/1984 | Bresler | 128/1.5 |
| 4,509,945 | 4/1985 | Kramann et al. | 604/164 |
| 4,526,177 | 7/1985 | Rudy et al. | 128/737 |
| 4,534,363 | 8/1985 | Gold | 128/772 |
| 4,552,157 | 11/1985 | Littleford | 128/786 |
| 4,572,198 | 2/1986 | Codrington | 128/653 |
| 4,602,645 | 7/1986 | Barrington et al. | 128/786 |
| 4,676,249 | 6/1987 | Arenas et al. | 128/657 |
| 4,739,768 | 4/1988 | Engelson | 128/658 |
| 4,771,788 | 9/1988 | Millar | 128/661.09 |
| 4,790,331 | 12/1988 | Okada et al. | 128/772 |
| 4,796,642 | 1/1989 | Harris | 128/772 |
| 4,809,713 | 3/1989 | Grayzel | 128/785 |
| 4,811,743 | 3/1989 | Stevens | 128/772 |
| 4,839,020 | 6/1989 | Yamaguchi et al. | 204/431 |
| 4,854,330 | 8/1989 | Evans, III et al. | 128/772 |
| 4,860,757 | 8/1989 | Lynch et al. | 128/657 |
| 4,880,414 | 11/1989 | Whipple | 604/283 |
| 4,884,573 | 12/1989 | Wijay et al. | 128/344 |
| 4,899,757 | 2/1990 | Pope, Jr. et al. | 128/662.06 |
| 4,905,698 | 3/1990 | Strohl, Jr. et al. | |
| 4,917,094 | 4/1990 | Lynch et al. | 128/657 |
| 4,925,445 | 5/1990 | Sakamotot et al. | 604/95 |
| 4,926,858 | 5/1990 | Gifford, III et al. | 606/159 |
| 4,932,419 | 6/1990 | de Toledo | 128/772 |
| 4,940,062 | 7/1990 | Hampton et al. | 128/772 |
| 4,975,546 | 12/1990 | Craig | 178/19 |
| 5,001,430 | 3/1991 | Peterman et al. | 324/326 |
| 5,005,592 | 4/1991 | Cartmell | |
| 5,014,008 | 5/1991 | Flowerdew | 324/326 |
| 5,040,543 | 8/1991 | Badera et al. | 128/772 |
| 5,042,486 | 8/1991 | Pfeiler et al. | |
| 5,078,714 | 1/1992 | Katims | 606/264 |
| 5,093,622 | 3/1992 | Balkman | 324/326 |
| 5,099,845 | 3/1992 | Besz et al. | |
| 5,119,028 | 6/1992 | Mooney et al. | 324/326 |
| 5,130,638 | 7/1992 | Furukawa | 324/67 |
| 5,146,916 | 9/1992 | Catalani | 128/207.14 |
| 5,171,228 | 12/1992 | McDonald | 604/175 |
| 5,183,045 | 2/1993 | Takamura et al. | 128/653.2 |
| 5,196,796 | 3/1993 | Misic et al. | 324/322 |
| 5,211,165 | 5/1993 | Dumoulin et al. | 128/653.1 |
| 5,253,653 | 10/1993 | Daigle et al. | 128/772 |
| 5,259,837 | 11/1993 | Van Wormer | 604/96 |
| 5,273,025 | 12/1993 | Sakiyama et al. | |
| 5,295,486 | 3/1994 | Wollschläger et al. | 128/661.01 |
| 5,316,024 | 5/1994 | Hirschi et al. | 128/899 |
| 5,325,873 | 7/1994 | Hirschi et al. | 128/899 |
| 5,345,945 | 9/1994 | Hodgson et al. | 128/772 |
| 5,375,596 | 12/1994 | Twiss et al. | 128/653.1 |
| 5,377,678 | 1/1995 | Dumoulin et al. | |
| 5,386,828 | 2/1995 | Owens et al. | 128/653.1 |
| 5,425,367 | 6/1995 | Shapiro et al. | |
| 5,425,382 | 6/1995 | Golden et al. | 128/899 |
| 5,429,132 | 7/1995 | Guy et al. | 128/653.1 |
| 5,513,637 | 5/1996 | Twiss et al. | |

CATHETER DEPTH, POSITION AND ORIENTATION LOCATION SYSTEM

RELATED APPLICATIONS

This application is a continuation in part of application Ser. No. 07/755,024, filed on Sep. 4, 1991, and issued on Jun. 20, 1995, as U.S. Pat No. 5,425,367, which is hereby incorporated by reference.

FIELD OF INVENTION

This invention relates to a system for locating the depth, orientation and position of a catheter inside biological tissue.

BACKGROUND OF INVENTION

In today's practice of medicine, catheters are routinely required to be positioned inside the human body. Catheters are frequently hollow tubes that infuse fluids into or extract fluids from body organs. Catheters may also contain conductive wires for delivering electrical impulses, such as pacemaker wires, or contain devices for sensing physiological functions such as temperature, blood pressure, and cardiac output. Catheters may contain optical fibers for observing the interior of body organs. A catheter may also be solid, such as a guide wire which is used to direct other catheters into body orifices, incisions or vessels.

Typically, catheters may be placed in the cardiovascular system, the digestive tract, the respiratory system, soft tissue, or other internal systems such as the excretory system. In most instances, catheters are placed using fluoroscopy or x-ray as a guide both during the procedure and as a confirmation that the device has been properly positioned. However, because of the cost of the equipment, fluoroscopy and x-ray are generally available only in the high cost operating room setting or in special procedure laboratories. Furthermore, there is a real concern about the repeated exposure of physicians, nurses and technicians to excessive radiation because of the multiple exposures required during placement and confirmation.

Two approaches to resolving these problems are disclosed in Van Steenwyck et al., U.S. Pat. No. 4,905,698. Van Steenwyck et al. disclose a catheter locating device which employs a sensing coil of wire embedded in the tip of a catheter tube, with the two coil wires brought out of the catheter to an external amplifier and detector circuit. The external probe contains two electromagnetic coils, one parallel to the skin (hereinafter called horizontal because the patient is generally in a supine position) and the other perpendicular to the skin (hereinafter called vertical), each driven by an electronic oscillator so that a high frequency magnetic field is generated by either coil. The device has a switch for alternatively energizing one or both of the coils. The sensing coil in the catheter senses the strength of the magnetic field generated by the horizontal (parallel) external coil, and the phase of the field generated by the vertical (perpendicular) external coil. The field strength at the sensor coil is inversely related to the distance between the horizontal coil and the sensor coil. The relative phase between the vertical coil drive signal and the resulting induced signal is indicative of the position of the vertical coil in relation to the sensor coil; the signals are in phase when the vertical coil is behind the sensor coil, the signals are out of phase when the vertical coil is in front of the sensor coil, and there is no induced signal in the sensor coil when the vertical coil is directly over the sensor coil.

Although the Van Steenwyck et al. device can relatively accurately locate the orientation and position of the catheter, it has a number of disadvantages which make it difficult and time consuming to use in the clinical setting. First, the device requires repeated scans with the probe parallel, then perpendicular, then rotated relative to the axis of the catheter. Further, the technique requires marking several external probe positions on the patient's skin and drawing a connecting line between them in order to establish the position of the sensor. Finally, the device requires switching repeatedly between the two external coils in order to verify the position and direction of the catheter sensor coil. Between 8 and 12 separate steps are necessary in order to establish the catheter position and direction. Furthermore, no quantitative indication of depth is given by the Van Steenwyck et al. device. The depth of the catheter below the surface of the skin can only be inferred from the signal strength displayed on the meter, and from the setting of the range-selector switch.

SUMMARY OF INVENTION

It is therefore an object of this invention to provide a system for externally locating the position, angular orientation and depth of a catheter which is simple and easy to use.

It is a further object of this invention to provide such a system which does not require repeated scans in a number of different directions.

It is a further object of this invention to provide such a system which does not require marking probe positions on the patient's skin.

It is a further object of this invention to provide such a system which does not require the operator to switch between coils.

It is a further object of this invention to provide such a system which completely eliminates the need for x-ray or fluoroscopy guidance during catheter placement.

It is a further object of this invention to provide such a system which gives a numerical display of the depth of the catheter below the skin, and a display indicating the direction in which the catheter is pointing.

This invention accomplishes the above objects, that is, an effective, easy to use catheter location system, by providing a pair of mutually perpendicular, coplanar, horizontal (parallel to the skin) electromagnetic coils driven alternately (sequentially) to generate a time-varying magnetic field. The field is detected by a sensor in the catheter. The system determines the depth of the catheter, independent of the relative angle between the probe axis in its horizontal plane and the angle of the sensor coil axis in its horizontal plane. When the probe is directly over the sensor, the strength of the signal induced in the sensor is related to the actual depth of the sensor below the probe.

This invention features a system for externally locating a sensor in tissue. The sensor is typically in a catheter inserted in the patient. The system is able to determine the depth of the sensor, and the direction in which the catheter tip is pointing, as well as locating the center of the sensor. These features may be provided in a small, handheld instrument which is moved by the physician over the patient's skin. The instrument, in one embodiment, provides an audible and/or visible signal when the instrument is located directly over the sensor in the catheter tip. At the same time, the depth of the catheter is displayed. There is also a display of the approximate true direction in which the catheter tip is pointing. This allows the user to ensure correct placement of the catheter carrying the sensor.

In one embodiment, the system includes an external probe which has at least first and second electromagnetic output coils with non-parallel longitudinal axes. In the preferred embodiment, there is a pair of mutually perpendicularly-oriented electromagnetic coils which are horizontal (parallel to the supine patient's skin), coplanar, and wound on a unitary cross-shaped core.

The system in this embodiment further includes an output coil driver means for alternately energizing the first and second output coils to generate a time-varying magnetic field outside of the patient's skin. The system further includes a sensor coil situated in the tip of a catheter, having a longitudinal axis, which develops an induced electrical signal in response to the time-varying magnetic field from the output coils in the external probe. There is a distance determinator, responsive to the induced signal generated by the sensor coil, for determining the distance between the output coils and the sensor coil, independently of the relative angle, in a horizontal plane, i.e., in a plane parallel to the output coils' axes, between the sensor projections into the horizontal plane of the coil longitudinal axis and the longitudinal axes of the output coils. Thus, the depth determination is not dependent on the angle between the sensor coil longitudinal axis and the longitudinal axis of either of the output coils.

The output coil driver means may alternately energize each of the at least two output coils with a high frequency drive signal. In one embodiment, the output coil driver means includes means for sequentially energizing a first, and then a second, of the output coils with a high frequency drive voltage, and then sequentially energizing the first and then the second output coils with the high frequency drive signal in reversed phase, to produce a virtual rotating magnetic field. In a second embodiment, the two output coils are alternately energized without phase reversal. By calculating the sum of the squares of the resulting induced sensor voltages, a value can be derived which is dependent on the distance between the sensor and the output coils, but independent of the sensor-probe horizontal angle.

The system may further include a distance display associated with the external probe for providing an output indicative of the distance between the external probe and the sensor.

The system preferably further includes a direction determinator for resolving the relative horizontal angle between the sensor coil longitudinal axis, and the longitudinal axis of at least one of the first and second electromagnetic output coils. The direction determinator may include means for calculating the tangent of the angle by dividing the induced sensor voltage caused by one output coil by the induced sensor voltage caused by the second output coil. The direction determinator may also include a phase comparison circuit for determining whether the voltage induced in the sensor by the first output coil is in phase or out of phase with the coil drive voltage for the first output coil. The phase comparison also determines whether the voltage induced in the sensor by the second output coil is in phase or out of phase with the coil drive voltage for the second output coil. There is preferably also included a visual display for displaying the true direction of the sensor coil longitudinal axis. The true direction is derived from the resolved relative horizontal angle, and indicates the actual direction in which the catheter tip is pointing.

For determining when the external probe is near or over a plane which bisects the sensor coil and is normal to the sensor coil longitudinal axis, the external probe may include a third electromagnetic output coil with a longitudinal axis which is transverse to the longitudinal axes of the first and second electromagnetic coils. Preferably, the third electromagnetic output coil longitudinal axis is vertical (axis perpendicular to the axes of both of the horizontal coils). The output coil driver means in that case energizes the third output coil with a third output coil high frequency drive voltage, for generating a second magnetic field which penetrates the patient's skin to induce an additional electrical signal in the sensor coil. There is a sensor coil position determinator which determines, from the third output coil high frequency drive voltage, and the additional electrical voltage induced in the sensor coil, when the longitudinal axis of the third output coil is proximate a plane bisecting the sensor coil and perpendicular to the sensor coil longitudinal axis. This sensor coil position determinator may be accomplished with a phase comparator for determining whether the third output coil drive signal is in phase or out of phase with the sensor coil voltage induced by the third coil magnetic field. The sensor coil position determination may be displayed with a display associated with the external probe which provides an output indicative of the determined position of the sensor coil in relation to the probe.

Alternatively, the sensor coil position determinator may be accomplished with a voltage determinator for determining the sensor coil voltage induced by the vertical output coil magnetic field. In this embodiment, the sensor coil position determinator may further include a storage device which stores the peak induced sensor voltage. The sensor coil position determinator may then further include means for establishing a voltage threshold value which is less than the stored peak voltage, and means for determining when the induced sensor voltage drops below the voltage threshold value. The voltage induced in the sensor coil by the vertical output coil drops as the external probe approaches the plane that bisects the sensor coil and is perpendicular to the longitudinal axis thereof at the midpoint of the sensor coil. Accordingly, the described arrangement determines when the longitudinal axis of the third output coil is approaching the plane bisecting the sensor coil. There may then further be included means for resolving when the induced sensor voltage rises at least a predetermined relative amount above the voltage threshold value after the induced voltage has dropped below the threshold value, for resolving when the longitudinal axis of the third output coil has moved farther from the plane bisecting the sensor coil. This sequence is thus an indication that the probe has approached and passed the plane. There may be included means for enabling the resolution of this voltage rise only within a specific time interval after the voltage has dropped below the voltage threshold, in order to reduce the likelihood of incorrect sensor coil midpoint determinations. This time interval is preferably adjustable. In one embodiment, there may further be included means for decaying the stored peak voltage over time, to also reduce the likelihood of incorrect sensor coil midpoint determinations. These features inhibit false readings which can occur at locations fairly distant from the sensor coil, at which the induced signal strength drops due to the distance between the output coil and the sensor coil.

In the preferred embodiment, the external probe includes two perpendicular, horizontally-oriented coils wound on a cross-shaped core, and a third, vertically-oriented coil. The coils of the horizontal coil pair are driven alternately with a high frequency voltage to generate a time-varying magnetic field which is sensed by the sensor coil wound coaxially very close to the tip of a catheter inserted in a patient. The vertical coil is also driven with a high frequency voltage. The same voltage may be used to drive all three coils if the coil drive voltages and the induced sensor coil voltages, are time-multiplexed. In this case, the induced sensor voltage is comprised of discrete segments which are induced by each of the two horizontal coils, and the vertical coil.

The sensor voltage induced by the horizontal output coils is related to the sensor-to-coil distance, and is also related to the horizontal angle of the sensor axis relative to the axis of the appropriate output coil. By sensing voltages induced by mutually perpendicular horizontal coils, and finding the vector sum of those signals, the resulting quantity is independent of the horizontal angle of the sensor axis relative to the axes of the output coils. Thus, a voltage is generated which is related to sensor-to-output coil distance, but is independent of the relative horizontal angular orientation of the probe and the sensor.

In the preferred embodiment, when the sensor midpoint is detected using the sensor voltage induced by the vertical coil, the sensor voltages induced by the horizontally-oriented output coils are measured, and the sensor true direction is calculated and displayed at the most accurate location.

BRIEF DESCRIPTION OF THE DRAWINGS

Other objects, features and advantages will occur to those skilled in the art from the following description of preferred embodiments and the accompanying drawings, in which.

DESCRIPTION OF THE PREFERRED EMBODIMENTS

This invention may be accomplished in a system for externally locating a sensor in tissue. The sensor is typically an inductive coil placed within a catheter near its tip. The system also includes an external, hand-held probe which generates electromagnetic fields which penetrate the patient's skin and couple to the sensor coil. The induced sensor coil voltages are detected. The sensor coil voltages, and the drive signals used to create the electromagnetic fields in the external probe, are compared, to determine the distance between the probe and the sensor coil, the relative angular orientation, in a horizontal plane, between the catheter and the probe, and to determine when the probe is directly over, or very close to, a plane bisecting the center of the sensor coil. The user thus is able to determine the location of the catheter tip, the depth of the catheter in the body, and the direction in which the catheter tip is pointing. This allows the user to confirm that the catheter tip is in the correct location, and pointing in the correct direction, to ensure proper catheter placement.

Figure 1:
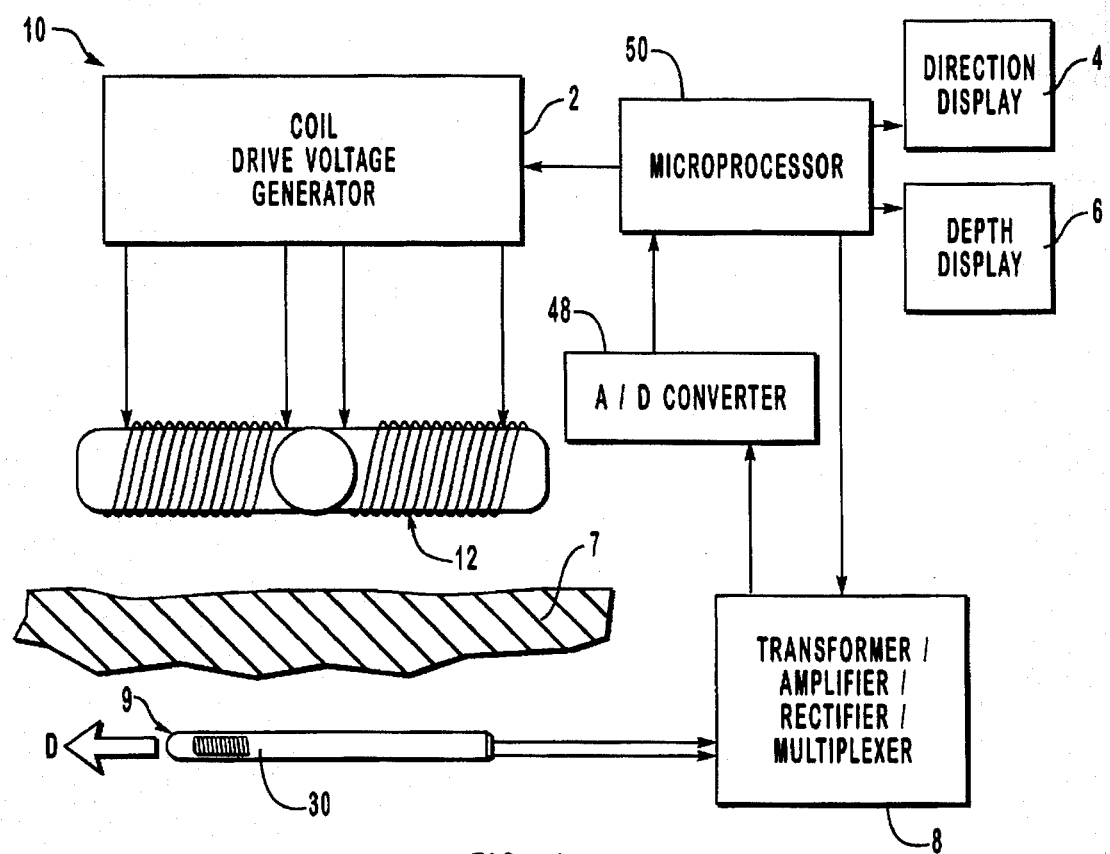
FIG. 1 is a simplified schematic block diagram of one embodiment of a catheter locating system according to this invention.

There is shown in FIG. 1 system 10 according to this invention for externally locating a sensor placed in a patient's body. System 10 includes an external probe which includes pair 12 of perpendicular electromagnetic output coils. Coil pair 12 is moved over skin 7 to detect the depth of, and angular orientation of, inductive sensor coil 30 carried by and proximate the distal end of catheter 9 located under skin 7.

The coils of coil pair 12 are driven by high frequency signals developed by coil drive voltage generator 2 under control of microprocessor 50. The coil drive voltages are preferably time-multiplexed to allow a single frequency source in microprocessor 50 to be used to generate the drive signals for both coils.

The electromagnetic fields generated from coil pair 12 penetrate skin 7 and induce voltages in sensor coil 30. These induced signals are transformed, amplified, rectified and multiplexed by transformer/amplifier/rectifier/multiplexer circuit 8. A transformer is used to isolate the patient from the input amplifier circuitry. The analog output signal of circuit 8 is then digitized by analog-to-digital (A/D) converter 48. The digitized signals are provided to microprocessor 50, which determines from these signals, and the drive signals provided to coil drive voltage generator 2, both the distance between coil set 12 and sensor coil 30, and the direction D (called the "true direction") in which the distal end of catheter 9 is pointing. The depth is displayed to the operator by depth display 6. The catheter true direction is displayed to the operator by direction display 4.

The use of an external probe with a pair of horizontal perpendicular output coils driven simultaneously with out of phase signals to create a virtual rotating magnetic field, a sensor coil which develops an induced electrical signal in response to the magnetic field generated by the output coils, and a distance determinator which determines, from the induced signal, the distance between the output coils and the sensor coil, independently of the relative horizontal angular orientation of the sensor coil axis and the axis of either of the output coils, is disclosed in copending application Ser. No. 07/755,024, filed on Sep. 4, 1991, incorporated herein by reference.

Figure 2A:
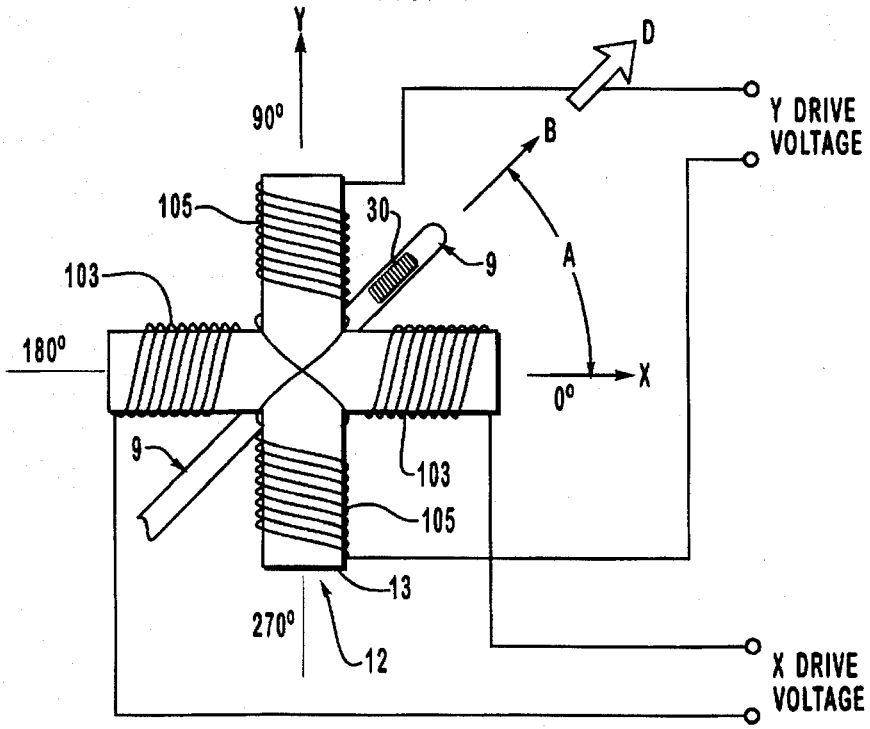
FIG. 2A is a schematic diagram of the pair of horizontal field generating coils located over the catheter of the system of FIG. 1, useful in illustrating the catheter depth determination accomplished by the system of this invention.

A preferred form of coil pair 12 is shown in more detail in FIG. 2A. Coil pair 12 includes cross-shaped coil form 13 on which are wound perpendicular, coplanar coils 103 and 105. Form 13 may be magnetic material or not. In the drawing of FIG. 2A, the longitudinal axis of coil 103 lies along an X-axis, and the longitudinal axis of coil 105 lies along a Y-axis. For convenience of reference hereinafter, coil 103 will on occasion be referred to as "the X coil," while coil 105 will on occasion be referred to as "the Y coil." Coil set 12 is shown as being almost directly above sensor coil 30 of catheter 9. Longitudinal axis X of coil 103 is non-parallel to longitudinal axis Y of coil 105. Preferably, the axes are perpendicular. Longitudinal axis B of sensor coil 30 lies at an angle A from axis X. The direction of the arrowhead on axis B also indicates the direction in which the distal end of catheter 9 is pointing (the true direction).

Coils 103 and 105 are driven separately by an X drive voltage and Y drive voltage, respectively, generated by coil drive voltage generator 2, FIG. 1. Together, coil drive voltage generator 2 and microprocessor 50 shown in FIG. 1 alternately energize coils 103 and 105. The distance determinator shown in FIG. 1 includes transformer/amplifier/rectifier/multiplexer 8, A/D converter 48, and microprocessor 50 which together determine from the voltage induced in sensor coil 30 the distance between sensor coil 30 and coils 103 and 105. Preferably, all of the components of system 10, with the exception of catheter 9, are carried by an external probe (not shown).

Coils 103 and 105 are alternately energized to generate a time-varying magnetic field which penetrates a patient's skin. In one embodiment, the time-varying magnetic field is created by first driving X coil 103, and then driving Y coil 105 with the same high frequency voltage. Coils 103 and 105 are then again sequentially driven by the same voltage, but reversed in phase in relation to the voltage used to drive the coils the first time. This scheme creates a magnetic field whose axis points in sequence to 0°, 90°, 180°, and then 270°. This pattern is repeated over and over to create a virtual rotating magnetic field. In another embodiment, which is the preferred embodiment which is employed in the remainder of the description of the preferred embodiments, coils 103 and 105 are driven alternately by the same drive voltage, without the phase reversal discussed above. This creates a magnetic field whose axis points in sequence to 0°, 90°, 0°, 90°, etc.

Because coils 103 and 105 are driven alternately without phase reversal, the voltage induced in coil 30 is related to both the sensor-to-coil distance, as well as the horizontal angle A of sensor axis B relative to X-coil 103 axis X, and Y-coil 105 axis Y. If Vsx is defined as the voltage induced in sensor coil 30 by the field from coil 103, and Vsy the coil 30 induced voltage from coil 105, those values may be determined by the following equations:

$$Vsx = K \cos A/d^3 \quad (1)$$

$$Vxy = KB \sin A/d^3 \quad (2)$$

where

Vsx=induced sensor voltage due to field from X coil
Vsy=induced sensor voltage due to field from Y coil
k=a constant A=horizontal angle between the projection of the axis of the sensor coil and the projection of the axis of the X coil into a plane parallel to the X and Y coils' axes
d=distance between sensor and output coils Vsx is thus a maximum when A=0°, and a minimum when A=90°. Conversely, Vsy is maximum when A=90°, and minimum when A=0°. The vector sum of Vsx and Vsy, is independent of angle A. If this vector sum is labelled Vsh, the following holds true:

$$Vsh = [Vsx^2 + Vsy^2]^{1/2} \quad (3)$$

Since $Vsh^2$ is in itself a quantity independent of angle A, it is not necessary to calculate the square root of the sum of the squares, as is done in equation (3). By not performing the square root calculation, the number of calculations required by microprocessor 50, FIG. 1, is reduced, allowing more time for other calculations to be performed by microprocessor 50.

Microprocessor 50 reads and stores the amplified, rectified Vsx and Vsy voltages, and performs the calculations of equations 1 through 3 to develop Vsh or $Vsh^2$. As explained below, microprocessor 50 then puts out digital information to drive depth display 6.

Figure 2B:
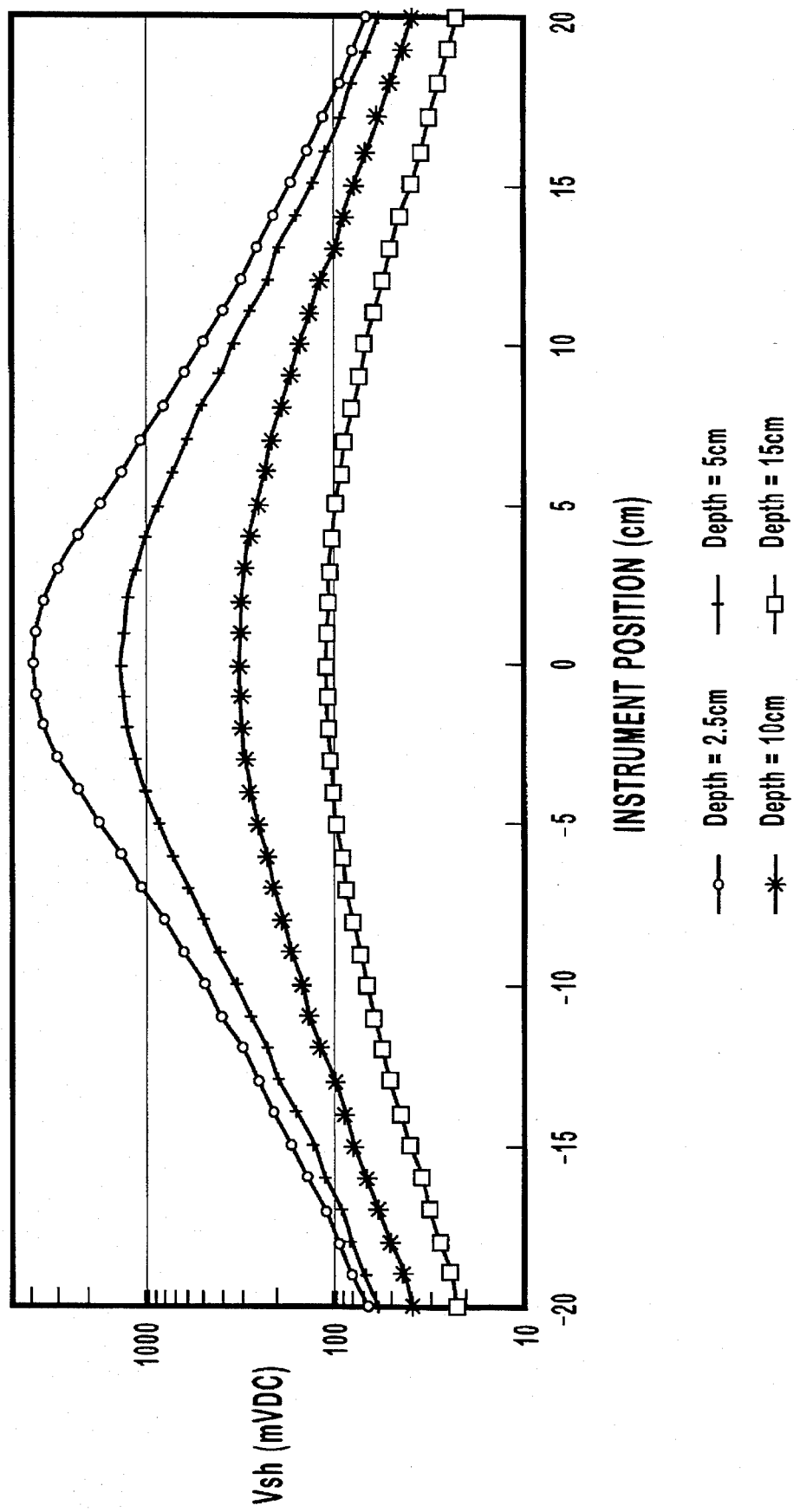
FIG. 2B is a graph of sensor coil voltage induced by the pair of horizontal field generating coils of FIGS. 1 and 2A, at four different catheter depths as the horizontal field generating coils are moved horizontally along the patient's skin.

FIG. 2B is a graph of instrument position versus Vsh. Note that the voltage values on the vertical axis are logarithmic. Shown are measurements taken at sensor coil depths below coil pair 12 of 2.5 cm, 5 cm, 10 cm, and 15 cm. These appear from the top to the bottom of FIG. 2B in the order just listed. Coil pair 12 was moved at right angles to the sensor coil longitudinal axis, starting at a position directly over the sensor coil (0 cm), out to 20 cm in either direction from the sensor coil longitudinal axis. As can be seen, the drawing of FIG. 2B illustrates that the induced sensor voltage is maximum when the output coils are directly over the sensor coil. As the coil pair is moved horizontally in a straight line at right angles to the sensor coil axis, the sensor voltage decreases as shown.

Figure 3:
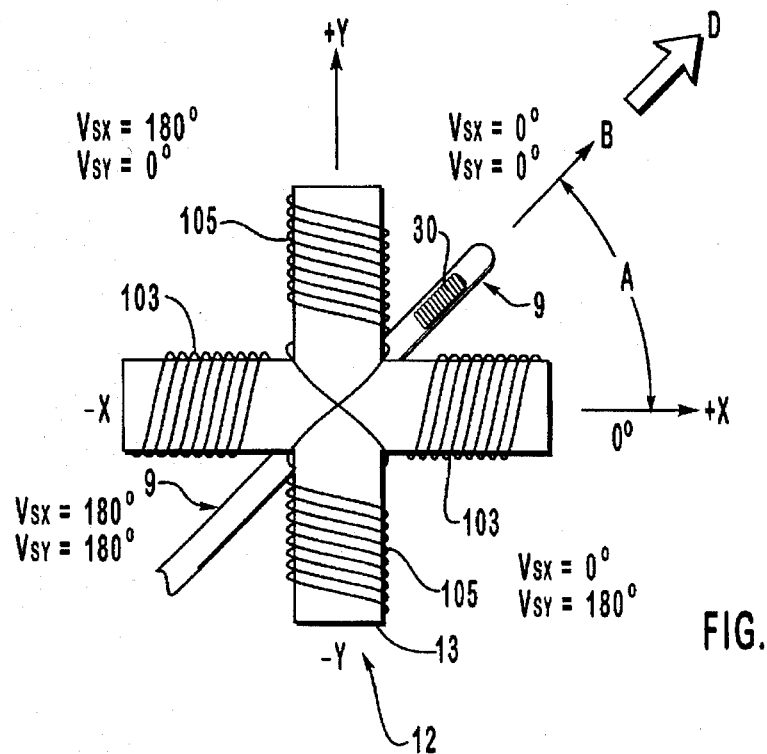
FIG. 3 is a view similar to that of FIG. 2A, illustrating the relative horizontal angular orientation of the sensor coil longitudinal axis, the longitudinal axes of the two horizontal field generating coils, and the phases of the induced sensor voltages relative to the phases of the respective output coil drive voltages.

It is also desirable for the system of this invention to determine the true direction D in which the catheter tip is pointing. This is the direction of arrow B, FIG. 2A, which may be defined in relationship to the direction of axis X or axis Y. As shown in FIG. 3, the direction of sensor coil longitudinal axis B (the true direction) may be defined by angle A between axis B and axis X of coil 103. Microprocessor 50 calculates angle A according to the following equation:

$$\tan A = Vsy/Vsx \quad (4)$$

where A is defined as the horizontal angle between sensor axis B and the X-coil axis X.

Angle A may lie in any one of the four quadrants defined by the X and Y axes. In order to determine the true direction in which the catheter tip is pointing, it is necessary not only to calculate the tangent of the angle A, but also to determine into which quadrant sensor coil 30 is pointing. This determination is made by measuring the phase between the voltage used to drive X coil 103, and the Vsx and Vsy voltages. When coil 30 is pointing to the positive X side of the Y axis, the phase difference between the X coil drive voltage and Vsx is 0 degrees. When output coil 30 is pointing to the negative X side of the Y axis, there is a 180° phase difference between those two voltages. Similarly, when sensor coil 30 is pointing to the positive Y side of the X axis, the Y coil drive voltage used to drive coil 105, and the voltage induced in the sensor coil from the Y coil voltage, are in phase (0 degrees). When sensor coil 30 is pointing to the minus Y side of the X axis, those two voltages are out of phase (180 degrees). Thus, by making the two phase comparisons, the quadrant is determined, which then fully defines the direction of longitudinal axis B in relation to longitudinal axis X, thus determining the catheter distal end true direction.

Figure 4A:
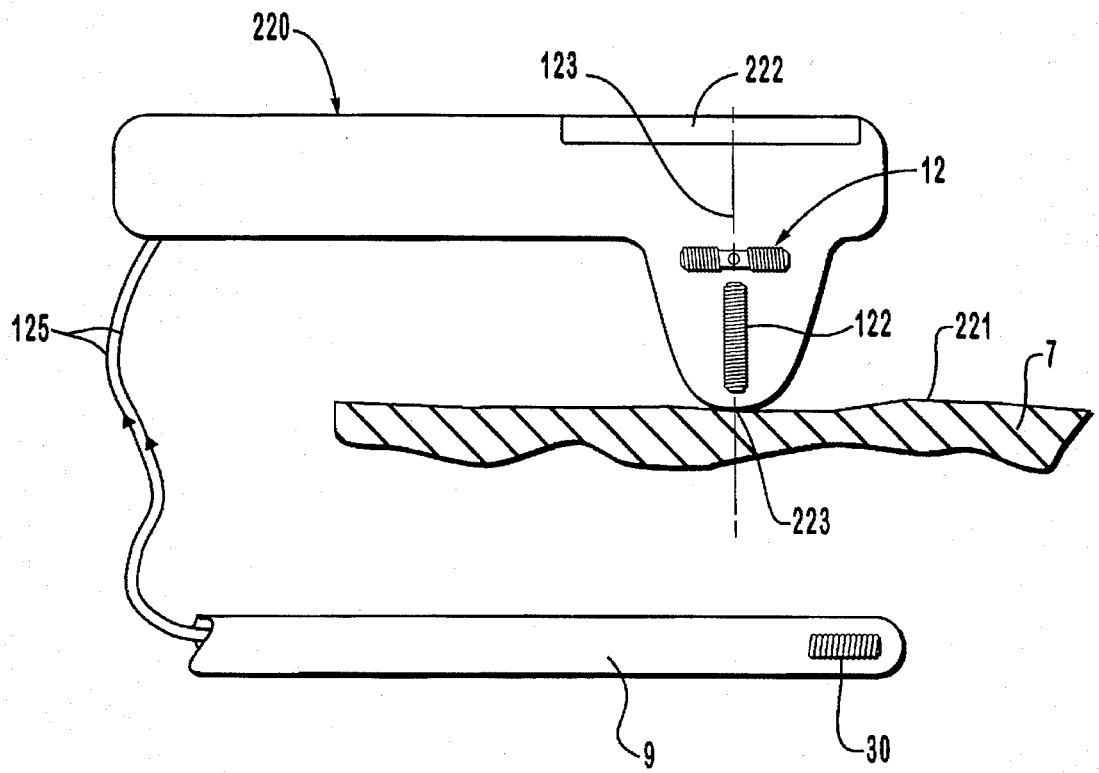
FIG. 4A is a cross sectional, schematic view of a catheter and one embodiment of the external probe of this invention that uses a vertically-oriented output coil.
Figure 4B:
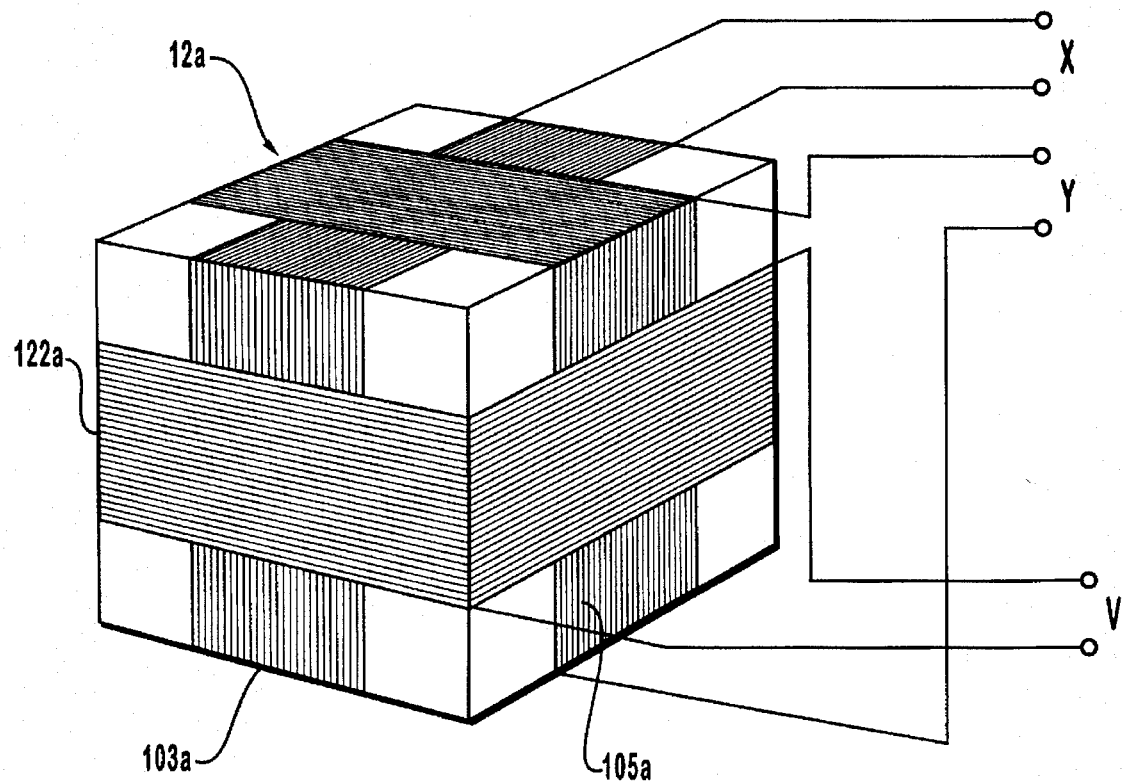
FIG. 4B is an alternate form of an output coil set incorporating a vertically-oriented output coil.

FIG. 4A is a cross sectional view through a preferred embodiment of the external probe 220 and the catheter 9 including sensor coil 30, of the system of this invention. FIG. 4A introduces an additional concept of a preferred embodiment of the system of this invention. Hand-held probe 220 includes horizontal coil pair 12 as described above relative to FIGS 2A and 3. Also included is vertically-oriented electromagnetic coil 122 which lies along "vertical" longitudinal axis 123, i.e., an axis transverse to a plane parallel to the axes of coils 103 and 105. FIG. 4B shows an alternate way of constructing coil set 12a to incorporate vertically oriented coil 122a and horizontal coils 103a and 105a. In use, probe 220 is held so that rounded probe tip 223 is on or next to the skin surface 221. As explained below, the probe is moved across surface 221 to locate sensor coil 30 near the distal end of catheter 9. Two wires 125 lead from catheter 9 to probe 220 to carry the signal induced in coil 30 by the magnetic fields generated from coil set 12 and vertical coil 122. Operator displays 222 mounted in probe 220 are described in more detail below.

Figure 5A:
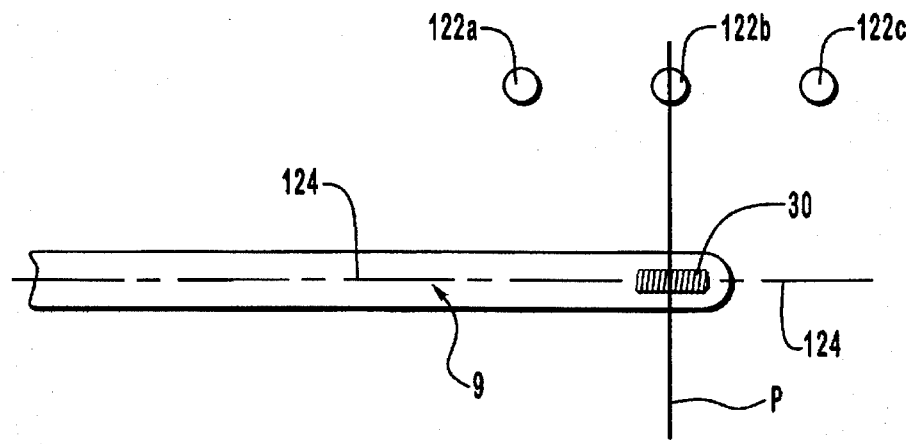
FIG. 5A is a view of the sensor showing an edge view of the plane which bisects the sensor midpoint.

Vertical coil 122, FIG. 4A, is used to determine when probe tip 223 is at or very close to plane P shown in FIG. 5A, which bisects sensor coil 30 and is perpendicular to longitudinal axis 124 of sensor coil 30. This embodiment of the system includes a sensor coil position determinator for determining, from the vertical output coil drive voltage, and the electrical voltage induced in sensor coil 30 by this vertical coil drive voltage, when the longitudinal axis 123 of vertical coil 122 is proximate plane P. This determines more exactly the position of sensor coil 30 in relation to probe 220. This determination can be made in two ways. The first way is to measure the phase change of the induced sensor voltage.

As vertical coil 122 moves from one side of plane P to the other, the phase of the voltage induced in sensor coil 30, in relation to the phase of the high frequency drive signal used to drive coil 122, changes from 0° (in phase) to 180° (out of phase). For example, when coil 122 is at position 122a on one side of plane P, FIG. 5A, the two signals are in phase. When coil 122 is at position 122c on the other side of plane P, the signals are out of phase. When coil 122 is at position 122b, in which longitudinal axis 123 of coil 122 lies in plane P, there would be no signal. However, in reality the induced sensor signal in this case would very quickly alternate between being in phase and out of phase with the output coil drive signal, as due to movement of the operator's hand, and slight movements of the sensor coil in the patient, coil 122 would never actually remain exactly centered on plane P.

Figure 5B:
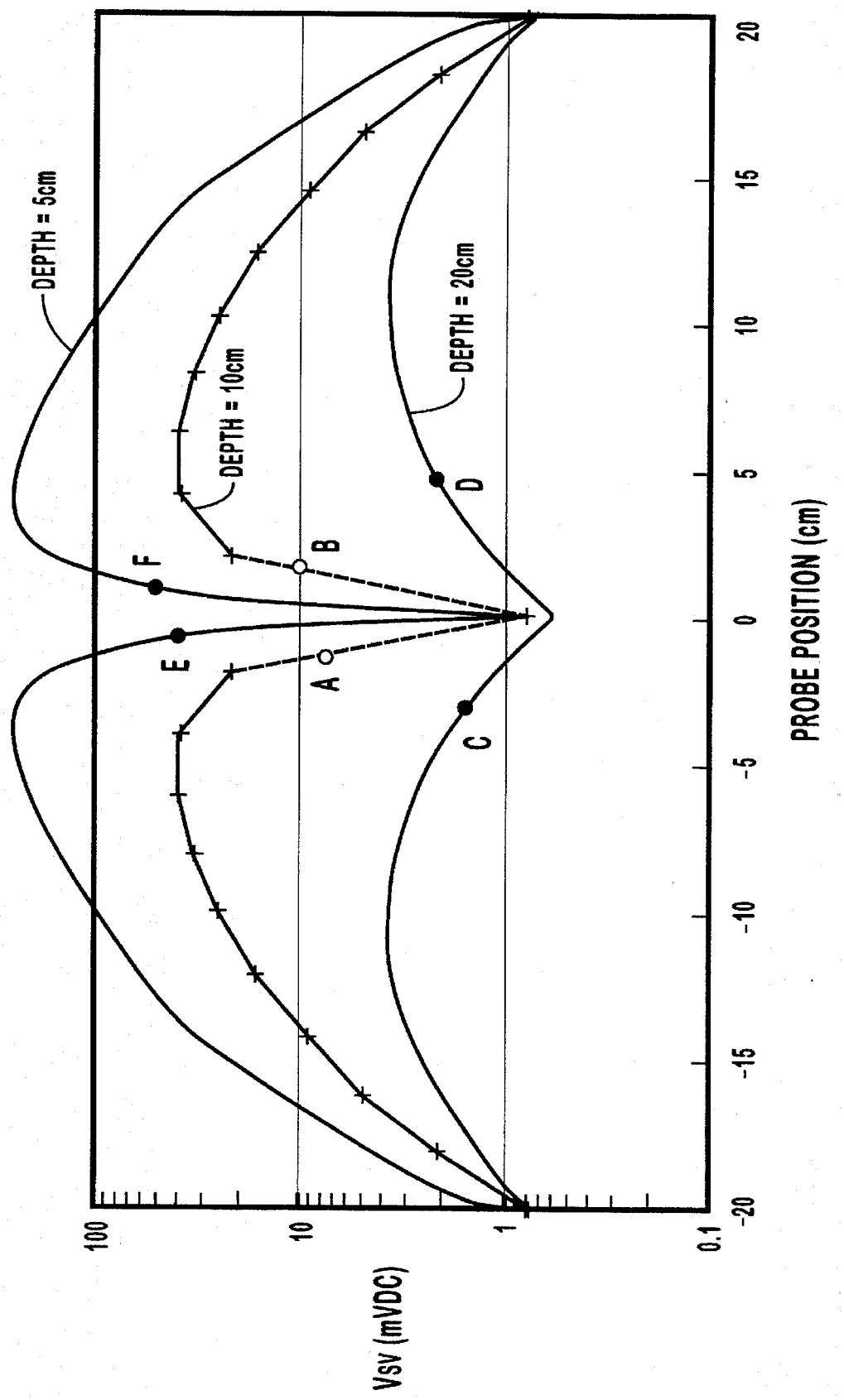
FIG. 5B is a graph of sensor coil output voltage induced by the vertical coil of FIG. 4 versus the distance of the vertical coil from the plane bisecting the sensor coil and perpendicular to the sensor coil longitudinal axis for three different sensor depths.

The second way to determine the position of sensor coil 30 in relation to probe 220 is to measure the change in amplitude of the induced sensor voltage. It has been found that the amplitude of the induced sensor voltage from the field generated from the vertical coil drops to a minimum, or a null, when the coil is directly over the plane P, (position 122b). As shown in FIG. 5B, the induced sensor voltage Vsv drops nearly to 0 when coil 122 is positioned in plane P. At a sensor coil depth of 10 cm, the voltage increases up to approximately 40 millivolts as the vertical coil is moved horizontally along axis 124, FIG. 5A, approximately 5 cm from plane P. Thus, the positioning of the vertical coil in relation to the sensor coil can also be determined from the sensor coil output voltage. Detection of plane P may thus be based either on the phase change between the vertical coil drive voltage and the resulting induced sensor voltage, or by detection of the sensor voltage null. Null detection, the preferred embodiment, is described in relation to FIGS. 6 through 9.

Figure 6:
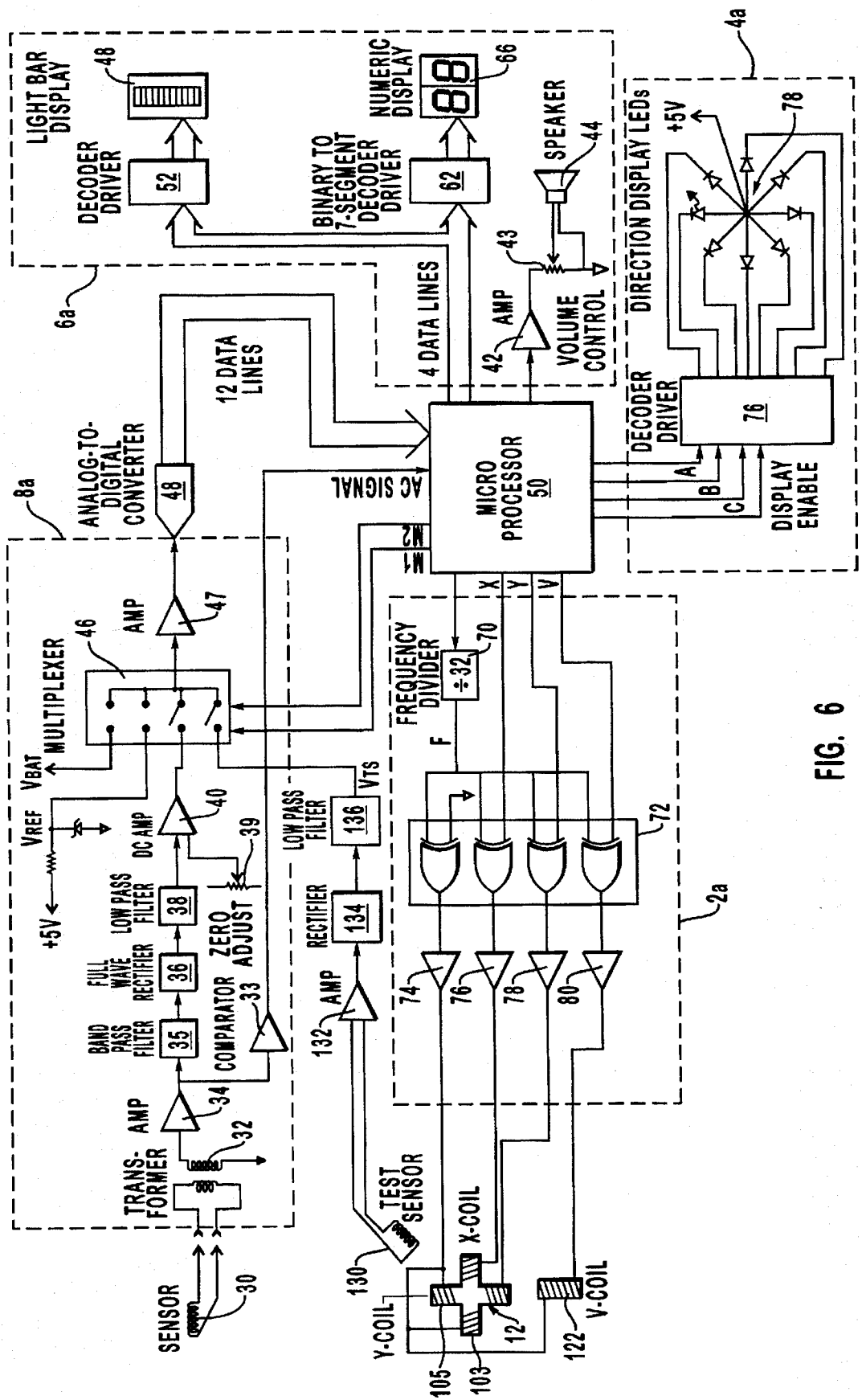
FIG. 6 is a schematic electronic diagram of the preferred embodiment of the system of this invention.
Figure 7:
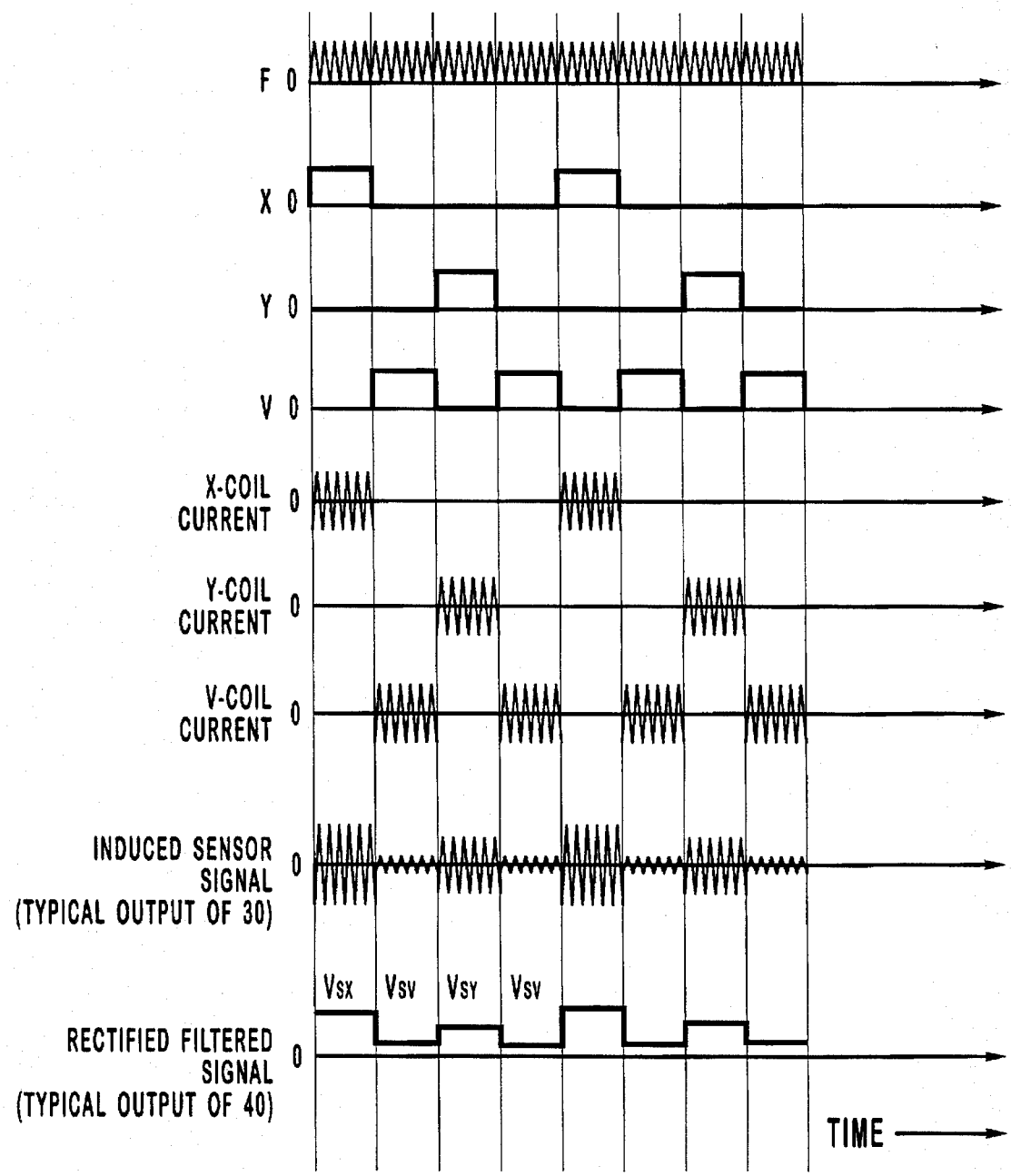
FIG. 7 is a timing diagram for the circuit of FIG. 6.

FIG. 6 is an electronic schematic diagram of the preferred embodiment of the system of this invention. Horizontal output coils 103 and 105 are wound on cross shaped core 12. Also shown is vertically-oriented coil 122. The coils are driven sequentially as shown in FIG. 7. Signal F is a high frequency drive voltage derived by dividing the clock frequency of microprocessor 50 using frequency divider 70. In one embodiment, the microprocessor 50 clock frequency is 2 Mhz, and the divider ratio is 32, resulting in a frequency of signal F=62.5 kHz. The sequence of coil drives is established by the output coil driver means which includes microprocessor 50, frequency divider 70, exclusive OR circuit 72, and amplifiers 74, 76, 78 and 80. Microprocessor 50 also has control outputs labelled X, Y, and V, shown in FIG. 7. These control signals are provided to circuit 72 to result in multiplexed high frequency drive signals which are amplified and provided to the appropriate coil as the X coil, Y coil and V coil currents depicted in FIG. 7. The vertical coil is thus energized after each time that either the X coil or Y coil is energized. The resulting voltages induced in sensor coil 30 are also shown in FIG. 7. In this example, the sensor voltage induced by the X coil current is larger than that induced by the Y coil current. For other sensor coil directions, the sensor voltage induced by the X coil current may be smaller than or equal to that induced by the Y coil current.

The induced sensor voltage is coupled through isolation transformer 32 to amplifier 34, band pass filter 35, full wave rectifier 36, low pass filter 38, and DC amplifier 40. Zero adjustment 39 ensures that the output of amplifier 40 is 0 volts when the sensor is positioned remotely from all three of the output coils, at a point where virtually 0 voltage is induced in the sensor. The output of amplifier 40 is connected to multiplexer 46, whose timing is controlled by signals M1 and M2 from microprocessor 50. The preferred multiplexing scheme is described below in conjunction with FIG. 9. The multiplexer output is connected to amplifier 47 which has a gain of 1. These components make up transformer/amplifier/rectifier/multiplexer circuit 8a. The rectified, filtered output signal of amplifier 40 is shown in the lowermost graph of FIG. 7.

Figure 8:
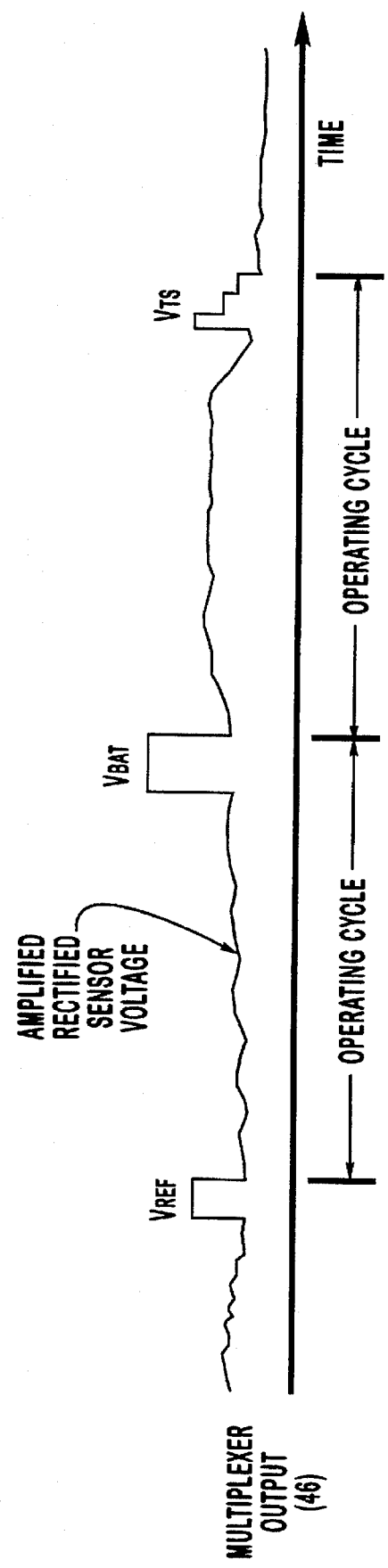
FIG. 8 depicts the multiplexer output for the system of FIG. 6, showing reference, battery, test sensor and sensor coil voltages.

As shown in FIG. 8, which is a graph of the output of multiplexer 46, the multiplexer is preferably timed to connect the amplifier 40 output voltage to amplifier 47 and then on to A/D converter 48 for the greater part of the measurement cycle. Multiplexer 46 is periodically connected to the battery voltage Vbat and precision DC voltage reference Vref, and to test sensor voltage Vts. In one embodiment, these three voltages are measured in sequence, once per second over three consecutive operating cycles. If the battery voltage Vbat drops below a predetermined threshold, microprocessor 50 is programmed to turn on a low battery indicator light. If the precision voltage reference Vref source changes value beyond a small tolerance, the microprocessor is preferably programmed to turn the instrument off.

Test sensor 130, FIG. 6, consists of a small inductive coil positioned adjacent to all three output coils. Typically, but not necessarily, its longitudinal axis is at a 45° angle to the longitudinal axes of all three output coils. The fields from each of the three output coils induce voltages in the test sensor which are amplified, rectified and filtered by amplifier 132, rectifier 134, and low pass filter 136, respectively. The resulting voltage Vts is periodically read by microprocessor 50. If an output coil should break, or if the coil drive current should fail or decrease beyond a preset limit, the test sensor output voltage Vts would change accordingly. The microprocessor is programmed to sense this and turn the instrument off to ensure that the instrument is on only when functioning properly.

Figure 11:
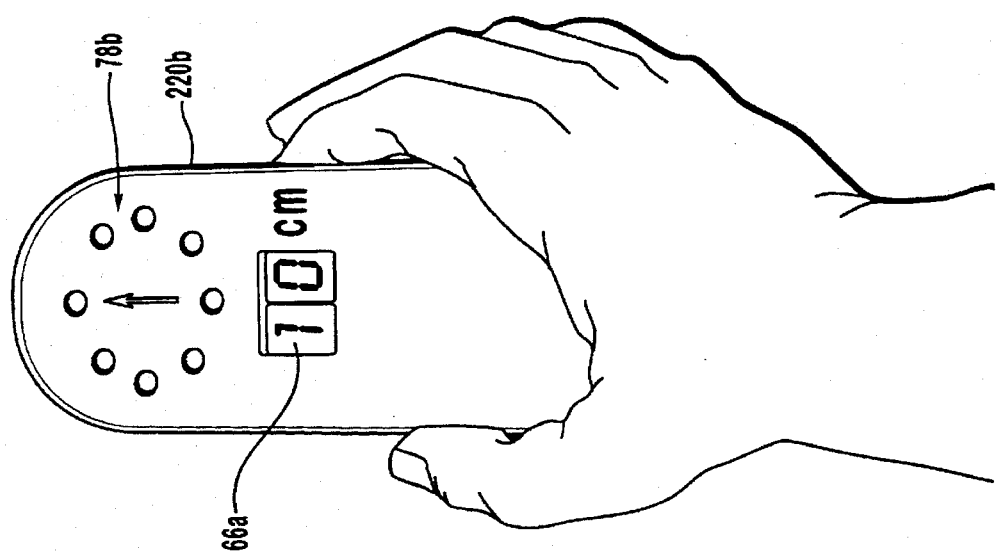
FIG. 11 is a top plan view of an alternative design for the external probe of the system of this invention.
Figure 10B:
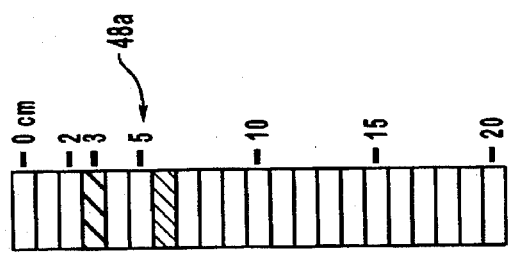
FIG. 10B is an enlarged view of the distance display of the probe of FIG. 10A.

The digital output of A/D converter 48 is connected to microprocessor 50. Microprocessor 50 is programmed to store the three voltage levels Vsx, Vsy and Vsv and perform the appropriate calculations to determine the sensor depth (distance from output coils 103 and 105 to sensor coil 30) and the true direction determined from angle A, FIGS. 2A and 3, as described above. The calculated values are then displayed as outputs to the operator. The preferred forms of the outputs are shown in FIG. 6 and also FIGS. 10A through 11.

Data establishing the sensor depth may be provided on four data lines to both decoder driver 52 and binary to seven-segment decoder driver 62. Driver 52 is enabled to drive light bar display 48, which may indicate the strength of the induced sensor voltage Vsh, shown in FIG. 2B. As described in the copending application incorporated herein by reference, light bar display 48a, FIGS. 10A and 10B, may be mounted on the upper surface of hand held probe 220a and include a number of segments which are typically LEDs with a scale of centimeters alongside. The minimum distance, which corresponds to the peak signal strength, is preferably continuously updated and the corresponding LED lit, along with the LED representing the currently-sensed distance, to give the operator a better idea of when the probe is closest to or directly over the sensor coil. Alternatively, numerical display 66, also shown as display 66a, FIG. 11, may be used to indicate the depth directly in inches or centimeters. The system converts Vsh (or $Vsh^2$) to distance by using the value of the variable to address a distance lookup table in microprocessor 50, FIG. 6. The lookup table stores numbers which convert to the depth (in inches, centimeters, or audio frequency).

Microprocessor 50 may also produce a variable frequency which is related to the induced sensor voltage and which is used to drive amplifier 42, which drives speaker 44 through volume control 43. This provides a tone whose frequency changes relative to the induced sensor voltage. This feature is also described in more detail in the copending application incorporated herein by reference.

Figure 10A:
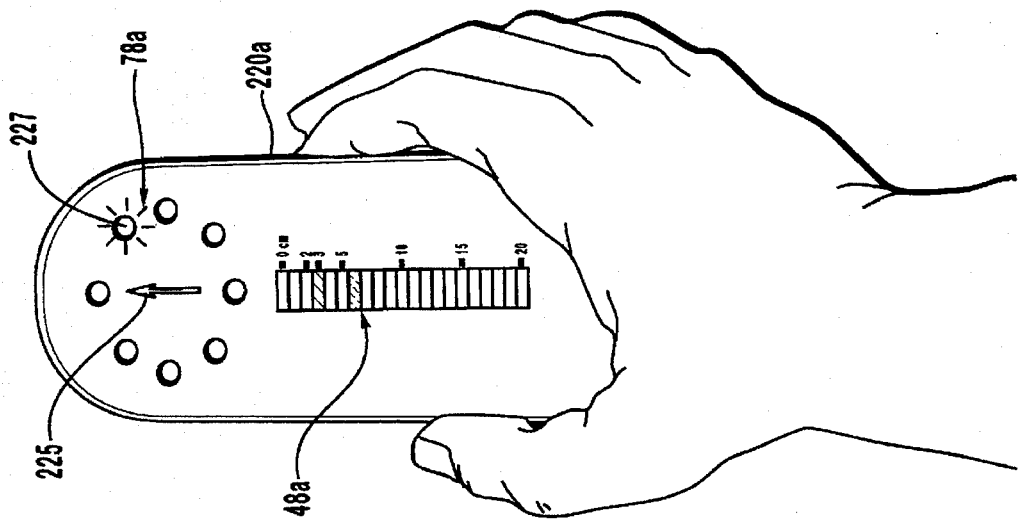
FIG. 10A is a top plan view of one form of an external probe for the system of this invention.

Direction display 78 in this embodiment consists of eight LEDs arranged in a circle as shown in FIG. 10A as direction display 78a. These LEDs are driven by decoder-driver 76, which converts digital information from microprocessor 50 to energize the appropriate direction-indicating LED such as LED 227, FIG. 10A. This direction display indicates that the distal end of the catheter is pointing in the direction of LED 227. This is the true direction in which the catheter distal end is pointing. This information is derived from the determination of angle A as described above in conjunction with FIGS. 2 and 3.

Figure 9:
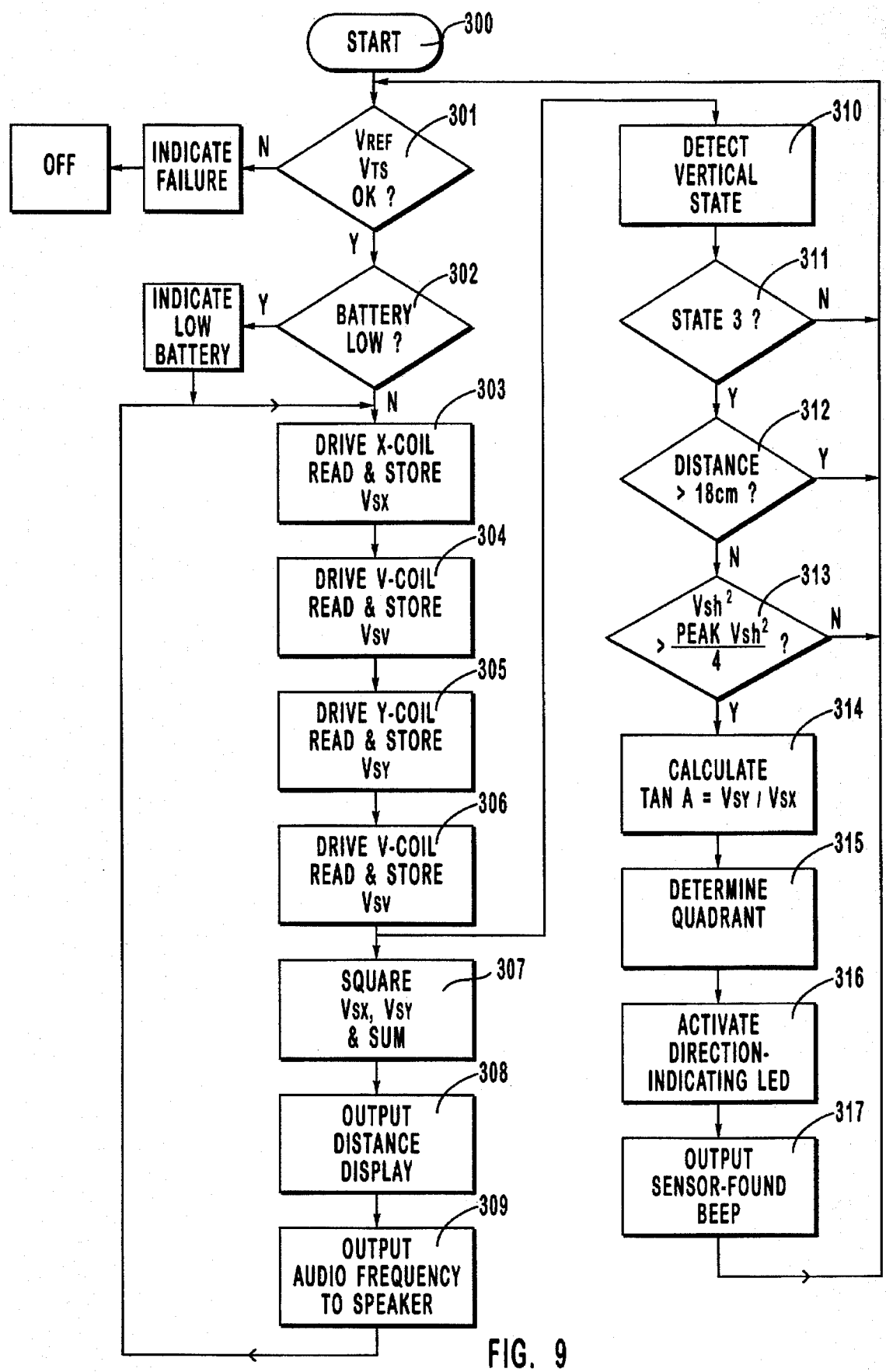
FIG. 9 is a flow chart illustrating the programming of the microprocessor of FIG. 6, and the operation of the system of FIG. 6.

FIG. 9 is a flow diagram of the preferred embodiment of the program resident in microprocessor 50, detailing the steps used to drive the three output coils, collect the sensor voltage level, make the necessary calculations and comparisons, and drive the audible and visual displays described above.

Start step 300 initializes all the storage registers and timers to zero, or to appropriate start up values. In step 301, multiplexer 46 is set by microprocessor 50 to select the reference DC voltage reference $V_{REF}$, and then select the amplified, rectified output of test sensor 130, Vts, and sequentially connect the voltages to A/D converter 48 shown in FIG. 6. If the values of the two voltages fall within preset limits, operation continues to step 302. Otherwise, a failure is indicated by alternately flashing the ON LED and the BATT.LOW LED for 15 seconds. The instrument is then shut off. In step 302, multiplexer 46 is connected by microprocessor 50 to the battery voltage Vbat. If Vbat is below a preset level, a low battery indicator, or LED, is activated by microprocessor 50. Operation would then continue to step 303.

In step 303, microprocessor 50 selects line X shown in FIG. 6 to drive X coil 105. Multiplexer 46 is enabled to select the amplified and rectified induced sensor voltage at the output of amplifier 40, which is digitized and stored in the memory of microprocessor 50. Steps 304, 305 and 306 repeat the process for the vertical coil by selecting line V out of the microprocessor 50, the Y coil by selecting line Y out of the microprocessor 50, and the vertical coil a second time, respectively.

In step 307, the signals induced by the X and Y coils are squared and summed by microprocessor 50 to produce a value which is based on the strength of the X and Y fields at the sensor, regardless of the sensor-to-output coil horizontal angle. In step 308, microprocessor 50 outputs from its lookup table digital information to drive decoder drivers 52 and 62 using the calculation as described above. At step 309, microprocessor 50 converts the values derived in step 307 to a variable frequency tone which drives speaker 44.

Steps 310 through 317 are the sensor coil location determination and direction display steps. In step 310, microprocessor 50 reads the value of the sensor coil voltage induced by the field generated from vertical output coil 122. Step 311 constitutes the microprocessor null detection subroutine for detecting the null in the output as shown in FIG. 5B. The microprocessor periodically reads and stores the peak value of the sensor voltage induced by the field from vertical output coil 122. Microprocessor 50 has established therein a threshold value which is a specific percentage of the peak vertical induced voltage. Typically, this threshold is set as ¼ of the peak voltage. Since the peak is continuously refreshed, this threshold may change. When the sensed voltage drops below this threshold, the microprocessor enters a second state—called state 2. After entering into the second state, if the vertical induced voltage again rises above the threshold by a predetermined amount, for example 50% above the threshold, state 3 is entered in step 311. If state 3 is entered, at step 312 the value of $Vsh^2$ is read. If the sensor-to-output coil distance determined from $Vsh^2$ is greater than a preset value (in this case 18 cm) the direction display is inhibited. This prevents the direction calculation from being based on weak induced signals which may have a large noise component and thus be inaccurate. In step 313, the microprocessor determines whether $Vsh^2$ exceeds the peak value of $Vsh^2$ divided by 4. If so, the tangent of angle A is calculated, step 314, the quadrant into which the sensor coil is pointing is determined, step 315, the appropriate direction-indicating LED is lit, step 316, and a "sensor found" audible beep is generated, step 317. This indicates to the operator that the sensor has been found. The direction calculation is performed only when the Vsv null has been detected (state 3). This is to ensure that the TangentA is calculated only when the XY output coil pair is closest to the sensor and at or near the plane of the sensor midpoint. This is where the tangent calculation is the most accurate.

As can be seen from FIG. 5B, if probe 220, which contains vertical coil 122, is moved back and forth relatively quickly while held at about 15 to 20 cm horizontally removed from the bisecting plane, at which there is a relative null in voltage $V_{sv}$, a false null may be simulated. That is, the voltage $V_{sv}$ can drop below the threshold and then rise again a percentage above the threshold. To reduce the likelihood of such a false null determination, microprocessor 50 is preferably programmed to require state 3 to occur within a specific required time interval after state 2 is entered, or else null detection is inhibited.

This state 2 to state 3 time interval is preferably variable with the strength of the peak voltage. For large sensor to output coil distances (depths), the peak signal is weak and the null is wide. That is, the voltage drops off relatively gradually as the vertical coil approaches plane P. In that case, a relatively long time interval is needed to allow the operator to move the instrument a sufficient distance to reach state 3. On the other hand, at shallow depths, the null becomes sharp and narrow. That is, the voltage drops off very rapidly when the output coil is very close to plane P. In this case, since the distance the probe must traverse to reach state 3 is small, the time interval can be short.

FIG. 5B illustrates this concept for three different catheter depths. At a depth of 10 cm, the probe must move from point A to point B to enter state 3. This equates to a distance of approximately 3 cm. If the probe is typically moved at 10 cm per second, the time interval to reach state 3 should be at least 0.3 seconds. At a depth of 20 cm, the distance from point C to point D is about 7 cm, which requires 0.7 seconds. Thus, the time interval should be at least 0.7 seconds. At shallow depths of 5 cm, only about 0.15 seconds is needed to traverse from point E to point F at the indicated speed. Thus, the time interval after state 2 is entered in which state 3 must be entered is preferably variable from about 0.15 to about 1.0 seconds. This time interval may be established by software in the microprocessor according to the peak value of Vsv using a lookup table.

In addition, the stored peak values of $Vsh^2$ and Vsv are preferably made to decay at a specific time constant, typically between 0.3 and 2.0 seconds. Decaying the Vsv peak helps to reduce false null determinations by continuously reducing the threshold values at distances remote from the sensor. If the decay time constant is too short, null detection can be inhibited if the operator is moving the instrument too slowly. If the decay constant is too long, false nulls can be indicated, if the operator moves the instrument back and forth at a horizontal distance of perhaps 15 to 20 cm from the sensor coil. Preferably the $Vsh^2$ peak is also decayed in a similar manner to ensure that null detection will not be inhibited if the operator should move the instrument slightly farther vertically from the sensor, thereby reducing Vsv while the same threshold voltage is maintained.

Although specific features of this invention are shown in some drawings and not others, this is for convenience only as each feature may be combined with any or all of the other features in accordance with the invention.

Other embodiments will occur to those skilled in the art and are within the following claims:

What is claimed is:

1. For externally locating a sensor in tissue, a system comprising:
    a) an external probe including at least first and second output coils having respective non-parallel first and second output-coil axes;
    b) an output coil-driver circuit that alternately so energizes the first and second output coils as to generate first and second time-varying magnetic fields that penetrate the tissue;
    c) a sensor coil that has a sensor-coil axis and develops first and second sensor signals in response to the first and second time-varying magnetic fields, respectively; and
    d) a distance determinator that determines from the first and second sensor signals, independently of the relative angles between the projection of the sensor-coil axis and the projections of the first and second output-coil axes into a plane parallel to the first and second output-coil axes, the distance between the sensor coil and the output coils and generates a distance signal representative of the distance thus determined.

2. A system as defined in claim 1 further including a distance indicator that receives the distance signal and generates a humanly perceptible indication of the distance represented thereby.

3. A system as defined in claim 1 further including:
    a) a test coil carried by the probe as to develop a test signal in response to at least one of the first and second time-varying magnetic fields; and
    b) a test circuit that receives the test signal and generates a fault indication if the test signal's magnitude is less than a predetermined minimum.

4. A system as defined in claim 1 further including a catheter in which the sensor coil is mounted.

5. A system as defined in claim 1 that further includes a direction determinator that determines from the first and second sensor signals the relative angle between the projection of the sensor-coil axis and that of at least one of the first and second output-coil axes into a plane parallel to the first and second output-coil axes and generates an angle signal representative of the angle thus determined.

6. A system as defined in claim 5 wherein the direction determinator determines the relative angle by computing a quantity proportional to a ratio of the first and second sensor signals.

7. A system as defined in claim 6 wherein:
    a) the output coil-driver circuit drives the first and second coils with time-varying signals with respect to which the first and second sensor signals have relative phases; and
    b) the direction determinator determines the relative angle additionally in accordance with those relative phases.

8. A system as defined in claim 5 further including a direction indicator that receives the angle signal and generates a humanly perceptible indication of the angle represented thereby.

9. A system as defined in claim 5 further including a catheter in which the sensor coil is mounted.

10. A system as defined in claim 1 wherein:
    a) the external probe includes a third output coil having a third output-coil axis transverse to a plane parallel to the first and second output-coil axes;
    b) the output coil-driver circuit further so energizes the third output coil as to generate a third time-varying magnetic field that penetrates the tissue;
    c) the sensor coil further develops a third sensor signal in response to the third time-varying magnetic fields; and
    d) the system further includes a sensor-coil-position determinator that determines from the third sensor signal whether the third output coil's axis is proximate a bisecting plane normal to the sensor-coil axis at the sensor coil's midpoint and generates a proximity signal indicative thereof.

11. A system as defined in claim 10 further including a distance indicator that receives the distance signal and generates a humanly perceptible indication of the distance represented thereby.

12. A system as defined in claim 10 wherein:
   a) the output coil-driver circuit drives the third coil with time-varying signals with respect to which the third sensor signal has a relative phase; and
   b) the sensor-coil-position determinator determines from that relative phase whether the third output coil's axis is proximate the bisecting plane.

13. A system as defined in claim 12 further including:
   a) a direction determinator that determines from the first and second sensor signals the relative angle between the projection of the sensor-coil axis and that of at least one of the first and second output-coil axes into a plane parallel to the first and second output-coil axes and generates an angle signal representative of the angle thus determined; and
   b) a direction indicator that receives the angle signal and generates a humanly perceptible indication of the angle represented thereby.

14. A system as defined in claim 13 wherein the direction indicator generates the humanly perceptible indication of the angle only when the proximity signal has indicated that the third output coil's axis is proximate the bisecting plane.

15. A system as defined in claim 12 further including a direction determinator that determines from the first and second sensor signals the relative angle between the projection of the sensor-coil axis and that of at least one of the first and second output-coil axes into a plane parallel to the first and second output-coil axes and generates an angle signal representative of the angle thus determined.

16. A system as defined in claim 15 wherein the direction determinator determines the relative angle only when the proximity signal has indicated that the third output coil's axis is proximate the bisecting plane.

17. A system as defined in claim 12 further including a proximity indicator that receives the proximity signal and generates a humanly perceptible indication thereof.

18. A system as defined in claim 17 wherein the humanly perceptible indication that the proximity indicator generates is an audible indication.

19. A system as defined in claim 10 further including a catheter in which the sensor coil is mounted.

20. A system as defined in claim 10 wherein the sensor-coil-position determinator determines that the third output coil's axis is proximate the bisecting plane by determining that a relative null has occurred in the magnitude of the third sensor signal.

21. A system as defined in claim 20 wherein the sensor-coil-position determinator establishes a first threshold equal to a predetermined fraction of a peak value of the third sensor signal's magnitude and determines that the relative null has occurred only if the third sensor signal's magnitude falls below the first threshold.

22. A system as defined in claim 21 wherein the sensor-coil-position determinator establishes a second threshold greater than the first threshold and determines that the relative null has occurred only if the third sensor signal's magnitude rises above the second threshold after falling below the first threshold.

23. A system as defined in claim 22 wherein the sensor-coil-position determinator determines that the relative null has occurred only if the third sensor signal's magnitude rises above the second threshold within a predetermined time interval after falling below the first threshold.

24. A system as defined in claim 23 further including means for adjusting the predetermined time interval.

25. A system as defined in claim 21 wherein the sensor-coil-position determinator reduces the first threshold over time.

26. A system as defined in claim 20 further including a proximity indicator that receives the proximity signal and generates a humanly perceptible indication thereof.

27. A system as defined in claim 26 wherein the humanly perceptible indication that the proximity indicator generates is an audible indication.

28. A system as defined in claim 20 further including a catheter in which the sensor coil is mounted.

29. A system as defined in claim 20 further including:
   a) a direction determinator that determines from the first and second sensor signals the relative angle between the projection of the sensor-coil axis and that of at least one of the first and second output-coil axes into a plane parallel to the first and second output-coil axes and generates an angle signal representative of the angle thus determined; and
   b) a direction indicator that receives the angle signal and generates a humanly perceptible indication of the angle represented thereby.

30. A system as defined in claim 29 wherein the direction indicator generates the humanly perceptible indication of the angle only when the proximity signal has indicated that the third output coil's axis is proximate the bisecting plane.

31. A system as defined in claim 20 further including a direction determinator that determines from the first and second sensor signals the relative angle between the projection of the sensor-coil axis and that of at least one of the first and second output-coil axes into a plane parallel to the first and second output-coil axes and generates an angle signal representative of the angle thus determined.

32. A system as defined in claim 31 wherein the direction determinator determines the relative angle when the proximity signal indicates that the third output coil's axis is proximate the bisecting plane.

33. For externally locating a sensor in tissue, a system comprising:
   a) an external probe including an output coil;
   b) an output coil-driver circuit that so energizes the output coil as to generate a time-varying magnetic field that penetrates the tissue;
   c) a sensor coil that has a sensor-coil axis and develops a sensor signal in response to the time-varying magnetic field; and
   d) a sensor-coil-position determinator that establishes a first threshold equal to a predetermined fraction of a peak value of the sensor signal's magnitude, makes a determination from the sensor signal of whether the output coil's axis is proximate a plane normal to the sensor-coil axis at the sensor coil's midpoint by determining whether a relative null has occurred in the sensor signal, and generates a proximity signal indicative of that determination, the proximity signal indicating that the relative null has occurred only if the sensor signal's magnitude falls below the first threshold.

34. A system as defined in claim 33 wherein the sensor-coil-position determinator establishes a second threshold greater than the first threshold and determines that the relative null has occurred only if the sensor signal's magnitude rises above the second threshold after falling below the first threshold.

35. A system as defined in claim 34 wherein the sensor-coil-position determinator determines that the relative null has occurred only if the sensor signal's magnitude rises above the second threshold within a predetermined time interval after falling below the first threshold.

36. A system as defined in claim 35 further including means for adjusting the predetermined time interval.

37. A system as defined in claim 33 wherein the sensor-coil-position determinator reduces the first threshold over time.

38. A system as defined in claim 33 further including a catheter in which the sensor coil is mounted.

39. For externally locating a sensor in tissue, a system comprising:
   a) an external probe including at least first and second output coils having respective non-parallel first and second output-coil axes;
   b) an output coil-driver circuit that alternately so energizes the first and second output coils as to generate first and second time-varying magnetic fields that penetrate the tissue;
   c) a sensor coil that has a sensor-coil axis and develops first and second sensor signals in response to the first and second time-varying magnetic fields, respectively;
   d) an analog-to-digital converter that responds to the sensor signals by generating digital signals representative thereof;
   e) a microprocessor that controls the output of the coil-driver circuit, that determines from the digital signals (1) the relative angle between the projection of the sensor-coil axis and that of at least one of the first and second output-coil axes into a plane parallel to the first and second output coil axes and, (2) independently of the relative angles between the projection of the sensor-coil axis and the projections of the first and second output-coil axes into a plane parallel to the first and second output-coil axes, the distance between the sensor coil and the output coils, and that generates angle and distance signals respectively indicative of the angle and distance thereby determined;
   f) a direction indicator that receives the angle signal and generates a humanly perceptible indication of the angle represented thereby; and
   g) a distance indicator that receives the distance signal and generates a humanly perceptible indication of the distance represented thereby.

40. A system as defined in claim 39 further including a catheter in which the sensor coil is mounted.

* * * * *